United States Patent
Wang

[11] Patent Number: 5,877,334
[45] Date of Patent: Mar. 2, 1999

[54] INTERMEDIATES USEFUL IN SOLID PHASE SYNTHESIS METHOD

[75] Inventor: Gary T. Wang, Niles, Ill.

[73] Assignee: Abbott Laboratories, Abbott Park, Ill.

[21] Appl. No.: 686,225

[22] Filed: Jul. 23, 1996

[51] Int. Cl.$^6$ .............................. C07C 53/134; C07F 7/04
[52] U.S. Cl. .................. 554/106; 554/219; 556/420; 556/440; 560/61; 560/183; 560/186; 560/25; 562/471; 562/587
[58] Field of Search .................................... 554/106, 219; 560/61, 183, 186, 25; 562/471, 587; 556/420, 440

[56] References Cited

FOREIGN PATENT DOCUMENTS

| 219300 | 4/1987 | European Pat. Off. . |
| 2729819 | 1/1978 | Germany . |
| 55-139842 | 11/1980 | Japan . |
| 2040853 | 2/1990 | Japan . |
| 93/19935 | 10/1993 | WIPO . |

OTHER PUBLICATIONS

G. T. Wang, et al. J. Med Chem, 38, No. 16, 2995–3002 Aug. 4, 1995.

J. Ellman, et al, J. Med Chem. 38 2995 (1995).

Greene TW & Wuts PGM, Protective Groups in Organic Synthesis. Second edition. John Wiley & Sons, INC. New York. pp. 224, 225, 231, 248, 1991.

McOmie JF.W. Protective Groups in Organic Chemistry. Plenum Press, London and New York. pp. 183–185, 1973.

Primary Examiner—Evelyn Huang

[57] ABSTRACT

A solid phase synthesis method and intermediates useful in the process are disclosed for the preparation of diamino diol and diamino alcohol inhibitors of HIV protease.

4 Claims, No Drawings

INTERMEDIATES USEFUL IN SOLID PHASE SYNTHESIS METHOD

This application claims the benefit of U.S. Provisional Patent Application No. 60/001,605, filed Jul. 28, 1995, which is incorporated herein by reference.

TECHNICAL FIELD

The present invention relates to a solid phase synthesis method useful for preparing compounds which are inhibitors of HIV protease. The present invention also relates to intermediates which are useful in the solid phase synthesis method.

BACKGROUND OF THE INVENTION

Drug discovery research involves the screening of large numbers of chemical compounds before a drug candidate is identified. One factor limiting the success of this process is the ability to rapidly synthesize compounds for testing in various screening assays. Recent advances in high throughput screening have increased the need for improved methods for rapid synthesis of compounds for testing.

Methods for solid phase synthesis of peptides have been used for many years to rapidly prepare peptides of various size and composition. Application of this technology to non-oligomeric small organic molecules could provide a method for rapid synthesis of large numbers of compounds. However, because such small organic molecules are not oligomeric and they frequently do not contain functional groups which lend themselves to coupling to solid phase supports, solid phase synthetic methods are not readily applicable.

HIV protease inhibitors are known to be useful for inhibiting HIV protease and for inhibiting an HIV infection in humans. The HIV protease inhibitors are an example of a class of compounds for which it is not obvious how solid phase synthetic methods can be readily applied.

In particular, the classes of HIV protease inhibitors represented by A77003 and A80987, and the like, present challenges for solid phase synthetic methods because (1) these molecules do not contain a functional group (typically, a carboxyl group) which can be used to attach the molecule to a solid support and (2) these molecules extend in both directions from the central diamino diol or diamino alcohol core unit, which is contradictory to the conventional unidirectional solid phase synthesis methods used to prepare peptides.

The HIV protease inhibitors A77003 and A80987 are disclosed in U.S. Pat. No. 5,142,056, issued Aug. 25, 1992 and U.S. Pat. No. 5,354,866, issued Oct. 11, 1994, respectively, both of which are incorporated herein by reference.

It has now been discovered that HIV protease inhibitors of the types represented by A77003 and A80987 can be readily synthesized using solid phase methods.

DISCLOSURE OF THE INVENTION

In accordance with the present invention, there are compounds of the formula IA:

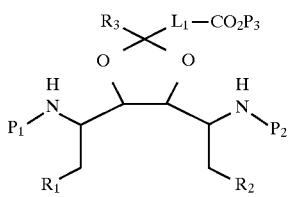

IA wherein $R_1$ and $R_2$ are independently selected from phenyl, substituted phenyl, loweralkyl and cycloalkyl; $R_3$ is hydrogen or loweralkyl; $L_1$ is alkylene; $P_1$ and $P_2$ are the same or different N-protecting groups; and $P_3$ is hydrogen or a carboxy protecting group; or a salt thereof.

Preferred compounds of the formula IA are compounds of the formula IB:

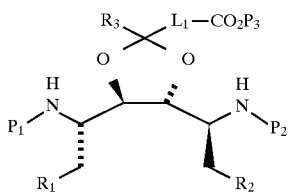

IB wherein $R_1$, $R_2$, $R_3$, $L_1$, $P_1$, $P_2$ and $P_3$ are as defined above.

Preferred compounds of formula IA and IB are those wherein $R_1$ and $R_2$ are phenyl, $R_3$ is $C_1$–$C_3$ alkyl and $L_1$ is —$(CH_2)_n$— wherein n is 2–6.

Even more preferred compounds of formula IA and IB are those wherein $R_1$ and $R_2$ are phenyl, $R_3$ is methyl and $L_1$ is —$(CH_2)_2$— and $P_1$ and $P_2$ are independently selected from 9-fluorenylmethoxycarbonyl, allyloxycarbonyl and (2-trimethylsilyl)ethoxycarbonyl and $P_3$ is hydrogen.

Compounds of the formula I can be prepared as shown in Scheme 1. The preferred compounds of the formula IB are shown as examples. Diol 1 is reacted with aldehyde or ketone 2 in the presence of an acid (for example, sulfuric

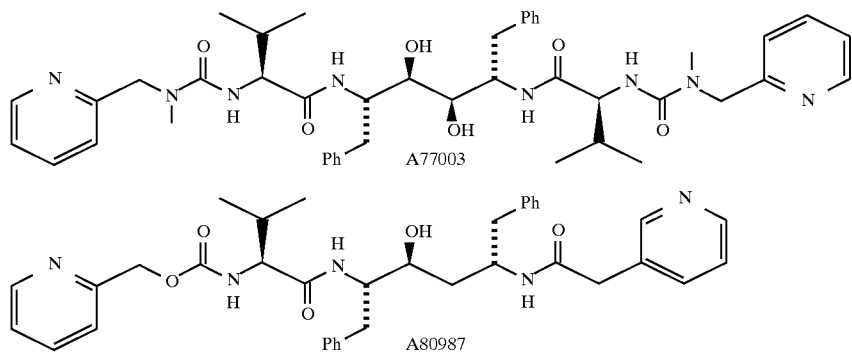

acid) to give IB. In diol 1, the N-protecting groups can be the same or different. For example, they can both be benzyloxycarbonyl (Cbz) groups. The Cbz groups can be removed (for example, by hydrogenation) and replaced with other N-protecting groups (for example, 9-fluorenylmethoxycarbonyl and the like) prior to coupling of IB (wherein $P_3$ is hydrogen) to a solid support (resin). Suitable resins include hydroxymethylphenoxymethyl resin (HMP resin or Wang resin), 4-methylbenzhydrylamine resin (MBHA resin), benzhydrylamine resin (BHA resin), chloromethyl resin (Merrifield resin) and the like. A preferred resin is NovaBead MBHA (4-methylbenzhydrylamine) resin (NovaBiochem, LaJolla, Calif.).

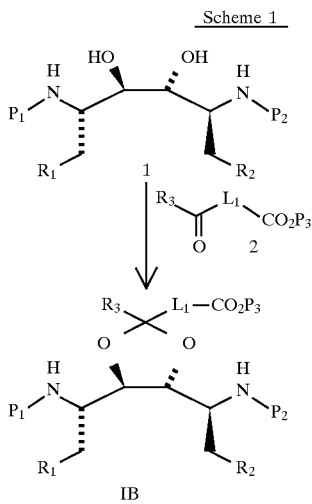

The compound of formula IA or IB can be used to prepare A77003 or analogs thereof by coupling IA or IB (wherein $P_3$ is hydrogen) to a solid support (resin) via an ester or an amide linkage (see Scheme 2 wherein IB is used as a specific example). A preferred coupling to a resin is via an amide bond. The N-protecting groups $P_1$ and $P_2$ are removed at the same time or separately and the left-hand and right-hand portions of the molecule are sequentially coupled to the core. For example, first an amino acid ($AA_1$) is coupled to each end using standard peptide coupling methodology, and then a terminating group (for example, a carboxylic acid (denoted by R—$CO_2H$)) is coupled to each end of the molecule using standard peptide coupling methodology. When $P_1$ and $P_2$ are different, selective deprotection allows different amino acids and different carboxylic acids to be added to each end of the core, resulting in non-symmetrical products. Acid-mediated cleavage (for example, with trifluoroacetic acid or the like) provides the desired product (7).

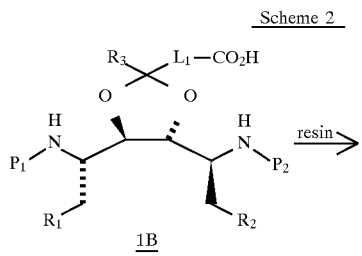

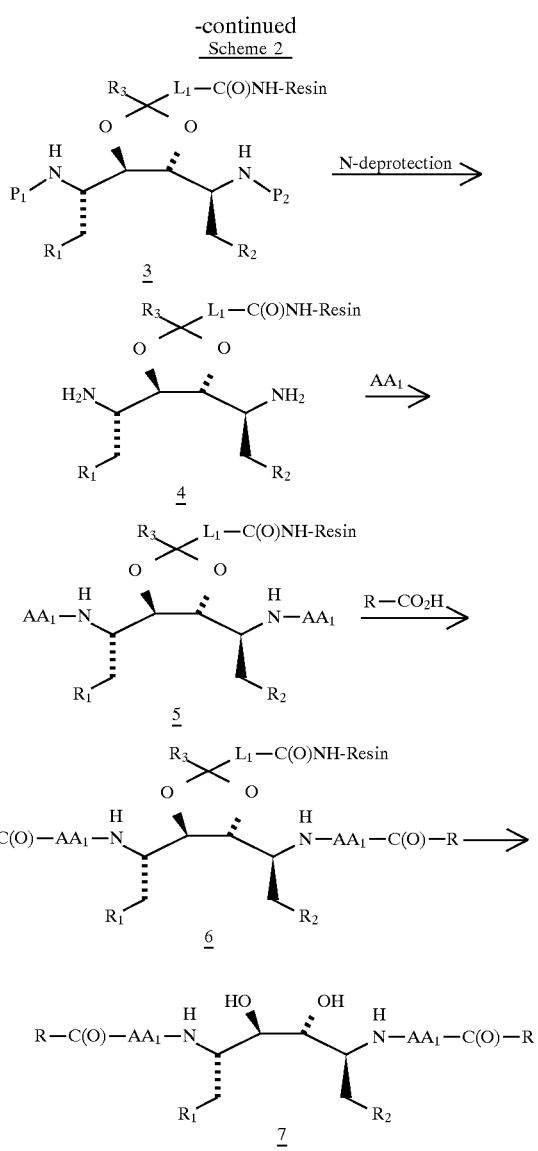

Also in accordance with the present invention, there are compounds of the formula IIA:

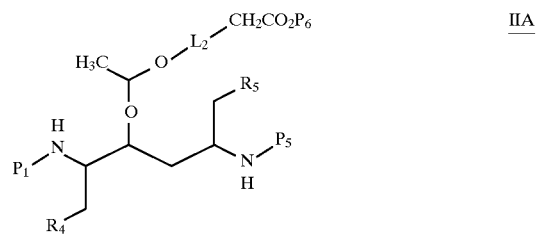

wherein $R_4$ and $R_5$ are independently selected from phenyl, substituted phenyl, loweralkyl and cycloalkyl;

$L_2$ is (a) alkylene, (b) —O—$((CH_2)_2—O)_m CH_2$— wherein m is 1–10 or

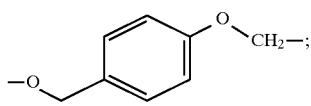 (c)

$P_4$ and $P_5$ are the same or different N-protecting groups; and $P_6$ is hydrogen or a carboxy protecting group; or a salt thereof.

Preferred compounds of the formula IIA are compounds of the formula IIB:

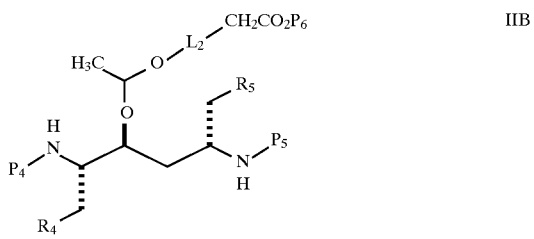 IIB wherein $R_4$, $R_5$, $L_2$, $P_4$, $P_5$ and $P_6$ are defined as above.

Preferred compounds of formula IIA and IIB are those wherein $R_4$ and $R_5$ are phenyl and $L_2$ is —$(CH_2)_p$— wherein p is 1–10 or —O—$((CH_2)_2—O)_m—CH_2$— wherein m is 2–6.

Even more preferred compounds of formula IIA and IIB are those wherein $R_4$ and $R_5$ are phenyl, $L_2$ is —$(CH_2)_9$— or —O—$((CH_2)_2—O)_2—CH_2$— and $P_4$ and $P_5$ are independently selected from 9-fluorenylmethoxycarbonyl, allyloxycarbonyl and (2-trimethylsilyl)ethoxycarbonyl and $P_6$ is hydrogen or allyl.

Also preferred are compounds of formula IIA and IIB wherein when $P_6$ is a carboxy protecting group, the carboxy protecting group can be selectively removed while retaining the N-protecting groups $P_4$ and $P_5$.

Also in accordance with the present invention, there are compounds of the formula III:

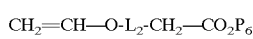 III wherein $L_2$ is
(a) alkylene,
(b) —O—$((CH_2)_2—O)_m—CH_2$— wherein m is 1–10 or

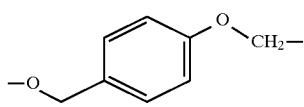 (c)

and $P_6$ is hydrogen or a carboxy protecting group.

Preferred compounds of formula III are those wherein $L_2$ is —$(CH_2)_p$— wherein p is 1–10 or —O—$((CH_2)_2—O)_m—CH_2$— wherein m is 2–6.

Even more preferred compounds of formula III are those wherein $L_2$ is —$(CH_2)_9$— or —O—$((CH_2)_2—O)_2—CH_2$— and $P_6$ is hydrogen or allyl.

Compounds of the formula III can be prepared as shown in Scheme 3. Carboxylic acid 8 is esterified (a preferred $P_6$ is allyl) to give ester 9. Reaction of 9 with ethyl vinyl ether and mercury acetate gives vinyl ether III.

Scheme 3

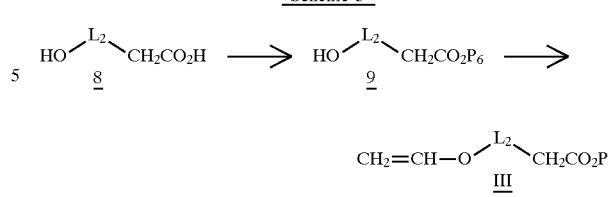

Compounds of formula II can be prepared as shown in Scheme 4 (using IIB as a specific example). Alcohol 10 is reacted with vinyl ether III in the presence of an acid catalyst (for example, pyridinium p-toluene sulfonate) to give IIB.

Scheme 4

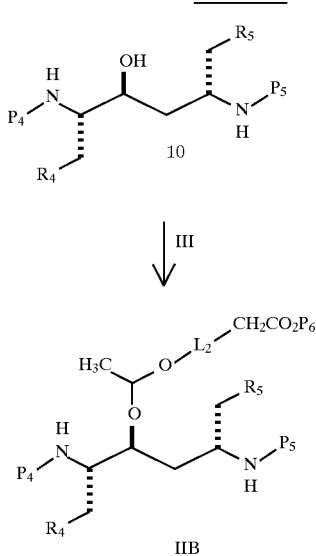

The compounds of formula IIA and IIB can be used to prepare A80987 or analogs thereof by coupling IIA or IIB (wherein $P_6$ is hydrogen to a solid support (resin) via an ester or amide linkage (see Schemes 5–6 wherein IIB is used as a specific example). A preferred coupling to a resin is via an amide bond. The N-protecting groups $P_4$ and $P_5$ are removed, at the same time or separately, and the left-hand and right-hand portions of the molecule are sequentially coupled to the core. For example, first an amino acid ($AA_1$) is coupled to each end using standard peptide coupling methodology and then a terminating group (for example, a carboxylic acid (denoted by R—$CO_2H$)) is coupled to each end of the molecule using standard peptide coupling methodology. When $P_4$ and $P_5$ are different, selective deprotection allows different amino acids and different carboxylic acids to be added to each end of the core, resulting in non-symmetrical products. Acid-mediated cleavage (for example, with trifluoroacetic acid or the like) provides the desired product (15).

To prepare non-symmetrical compounds directly analogous to A80987, one starts with compound 11 wherein $P_4$ and $P_5$ can be selectively removed (for example, $P_4$ is 9-fluorenylmethoxylcarbonyl (Fmoc) and $P_5$ is allyloxycarbonyl). $P_4$ is removed and $AA_1$ is coupled, followed by R—$CO_2H$. Then $P_5$ is removed and R'—$CO_2H$ is coupled to give 19.

Scheme 5
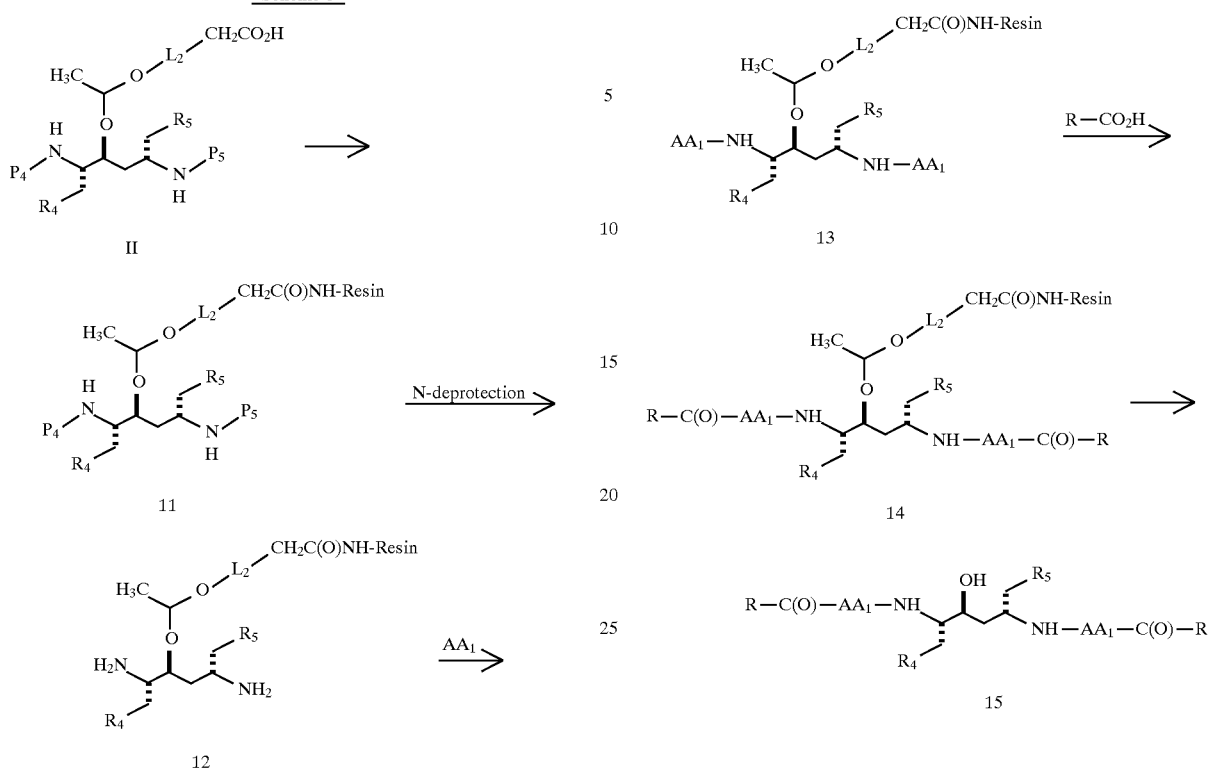
Scheme 6
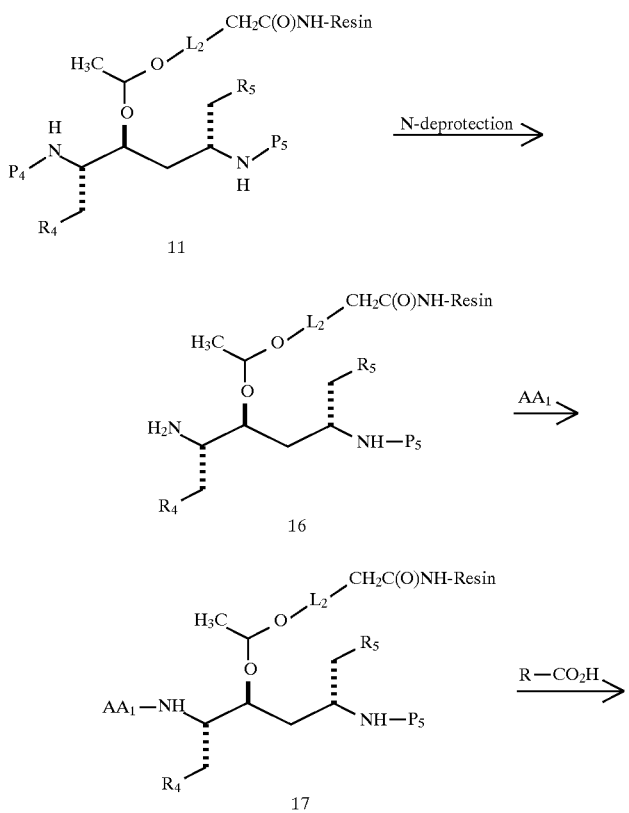

-continued
Scheme 6

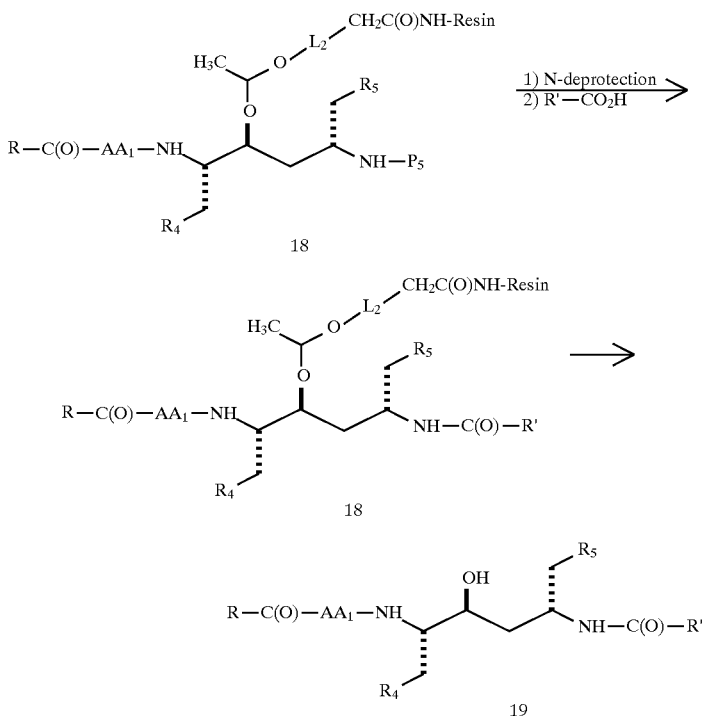

Compounds of the invention comprise asymmetically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30.

The term "loweralkyl" as used herein refers to straight or branched chain alkyl radicals containing from 1 to 10 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "alkylene" as used herein refers to a straight or branched chain carbon diradical containing from 1 to 10 carbon atoms including, but not limited to, —CH$_2$—, —CH$_2$CH$_2$—, —CH(CH$_3$)CH$_2$—, —CH$_2$CH$_2$CH$_2$—, and the like.

The term "substituted phenyl" refers to a phenyl group which is substituted with one, two or three substituents independently selected from loweralkyl, alkoxy, halo, thioalkoxy, amino, alkylamino, dialkylamino and hydroxyalkyl.

The term "hydroxyalkyl" as used herein refers to —OH appended to a loweralkyl radical.

The term "alkylamino" as used herein refers to a loweralkyl radical appended to an NH radical.

The terms "alkoxy" and "thioalkoxy" as used herein refer to R$_{29}$O— and R$_{29}$S—, respectively, wherein R$_{29}$ is a loweralkyl group.

The term "dialkylamino" as used herein refers to —NR$_{36}$R$_{37}$ wherein R$_{36}$ and R$_{37}$ are independently selected from loweralkyl groups.

The term "halo" or "halogen" as used herein refers to —Cl, —Br, —I or —F.

For the purpose of this application, the symbol P refers to either a protecting group or the absence of a protecting group. An ordinary practioner would know that phosphorus is a tri-valent or penta-valent atom and that lack of substituents thereto would indicate fiat the P$_1$, P$_2$, P$_3$, P$_4$, P$_5$, and P$_6$ designations in the specification and the claims have meanings other than the symbol for phosphorus.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in Greene, "Protective Groups in Organic Synthesis" pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); haloalkyl; alkenyl; cycloalkyl and substituted derivatives thereof such as cyclohexyl, cylcopentyl and the like; cycloalkylalkyl and substituted derivatives thereof such as cyclohexylmethyl, cylcopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups In Organic Synthesis," (John Wiley & Sons, New York (1981)), which is hereby incorporated herein by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl, (2-trimethylsilyl)ethyloxycarbonyl and the like; alkyl groups such as benzyl, triphenylmethyl, benzyloxymethyl and the like; and silyl groups such as trimethylsilyl and the like. Preferred N-protecting groups are 9-fluorenylmethoxycarbonyl, allyloxycarbonyl and (2-trimethylsilyl)ethyloxycarbonyl.

Salts of the compounds of the present invention indlude salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The foregoing may be better understood by reference to the following examples which are provided for illustration and are not intended to limit the scope of the inventive concept.

EXAMPLE 1

(4R, 5R, 1"S)-1-Methyl-1-(3'-carboxypropyl)-4, 5-bis[1"-(benzyloxycarbonyl)amino-2"-phenyl]ethyl-1, 3-dioxolane A suspension of (2S,3R,4S,5S)-2,5-di-(Cbz-amino)-3,4-dihydroxy-1,6-diphenylhexane (10.0 g, 17.62 mmole; U.S.

Pat. No. 5,142,056, issued Aug. 28, 1992) in 60 mL of levulinic acid and 0.8 mL of conc. $H_2SO_4$ was stirred at ambient temperature for 24–48 hours, or until the mixture turned into a homogeneous yellow solution. The reaction mixture was taken up in 200 mL of ether and the solution was washed repeatedly with saturated NaCl solution to remove excess levulinic acid. Upon complete removal of levulinic acid (TLC), the etheral solution was dried ($MgSO_4$), filtered, evaporated and dried in vacuo to give a white solid. 11.43 g, 97.3%. $^1$H NMR ($CDCl_3$) $^1$H NMR ($CDCl_3$): δ 1.40 (s, 3H), 2.0–2.1 (m, 2H), 2.35–2.50 (m, 2H), 2.70–2.90 (m, 4H), 3.65–3.75 (m, 2H), 3.95 (m, 1H), 4.10 (m, 1H), 4.70–5.00 (m, 6H), 7.00–7.30 (m, 20H); FAB-MS m/z 667 $(M+H)^+$, 623 $(M-CO_2)^+$, base peak.

EXAMPLE 2

(4R, 5R, 1"S)-1-Methyl-1-(3'-carboxypropyl)-4, 5-bis[1"-amino-2"-phenyl]ethyl-1,3-dioxolane The product of Example 1 (11.4 g, 17.14 mmole) was hydrogenated in EtOAc or MeOH with 10% Pd/C as the catalyst at ambient temperature. The catalyst was filtered and washed extensively with MeOH. Concentration of the solution gave 6.64 g (97.2%) of a white solid. $^1$H NMR (MeOH-$d_4$): δ 1.40 (s, 3H), 2.10 (m, 2H), 2.30 (m, 2H), 2.55–2.70 (m, 2H), 2.90 (d, 2H), 3.10 (m, 1H), 3.45 (m, 1H), 3.95 (m, 1H), 4.10 (m, 1H), 7.10–7.40 (m, 10H); CIMS m/z 399 $(M+H)^+$, base peak.

EXAMPLE 3

(4R, 5R, 1"S)-1-Methyl-1-(3'-carboxypropyl)-4, 5-bis[1"-[(fluorenylmethyloxy)carbonyl]amino-2"-phenyl]ethyl-1,3-dioxolane To a solution of the product of Example 2 (3.79 g, 9.52 mmole), a mixture of 55 mL of dioxane and 50 mL of water containing sodium bicarbonate (1.639 g, 19.5 mmole) was added a solution of Fmoc-OSu (NovaBiochem, 6.48 g, 19.23 mmole) in 50 mL of dioxane over several minutes. After stirring at ambient temperature overnight, water (300 mL) was added and the mixture was carefully acidified to pH 2 with 1N HCl and extracted with EtOAC (5×100 mL). The combined organic solution was worked up routinely and evaporated to give an off-white solid. Column chromatography using 60% EtOAc in hexane as the solvent afforded 7.5 g (93.5%) of the title compound as a white solid. $^1$H NMR (MeOH-$d_4$): δ 1.48 (s, 3H), 1.98 (d, 2H), 2.10 (t, 2H), 2.48 (m, 2H), 2.80 (m, 4H), 3.90–4.15 (m, 8H), 6.8–7.8 (m, 26H). FAB-MS m/z 843 $(M+H)^+$, 881 $(M+K)^+$.

EXAMPLE 4A

Allyl 10-Hydroxydecanoate

To a solution of 10-hydroxydecanoic acid (5.0 g, 26.5 mmole) and allyl alcohol (15.5 g, 265 mmole) in 100 mL of $CH_2Cl_2$ was added 1-ethyl-3-(3-dimethylaminopropyl) carbodiimide hydrochloride (Sigma Chemical Co., 6.15 g, 31.8 mmole) and DMAP (100 mg). After stirring for 2 h, the solution was washed with 0.1N HCl (3×50 mL), 5% aqueous $NaHCO_3$ (3×50 mL), and brine (3×50 mL), then dried ($MgSO_4$), filtered and concentrated. The crude product was passed through a silica gel plug using 40% EtOAc in hexane to remove the baseline contamination. Concentration of the solution gave 4.5 g of an oil (75.0%). $^1$H NMR ($CDCl_3$): δ 5.92 (m, 1H), 5.32 (d,q, 1H), 5.23 (d,q, 1H), 4.58 (d.t, 2H), 3.63 (t, 2H), 3.65 (T, 2H), 2.35 (t, 2H), 1.5–1.7 (m, 4H), 1.3 (m, 8H). CIMS ($NH_3$) m/z 229 $(M+H)^+$, 246 $(M+NH_4)^+$.

EXAMPLE 4B

Allyl 10-Vinyloxydecanoate

Mercury acetate (2.44 g, 7.7 mmole) was added to a solution of allyl 10-hydroxydecanoate (3.5 g, 15.4 mmole) in 80 mL of distilled ethyl vinyl ether. The solution was purged with argon and refluxed under argon atmosphere overnight. After cooling to ambient temperature, $K_2CO_3$ (1.0 g) was added and the mixture stirred for 30 minutes. EtOAc (100 mL) was added and the solution was washed with saturated NaCl (4×80 mL), then dried (($MgSO_4$), filtered and concentrated. The residue was purified by column chromatography using 30% EtOAc-hexane as the solvent to give 3.0 g of a liquid (61%). $^1$H NMR ($CDCl_3$): δ 6.45 (d.d, 1H), 5.92 (m, 1H), 5.32 (d.q, 1H), 5.23 (d.q, 1H), 4.58 (d.t, 2H), 4.18 (d.d, 1H), 3.97 (d.d, 1H), 3.63 (t, 2H), 2.35 (t, 2H), 1.5–1.7 (m, 4H), 1.3 (m, 8H). CIMS ($NH_3$) m/z 255 $(M+H)^+$, 272 $(M+NH_4)^+$.

EXAMPLE 4C (2S, 3S, 5S)-3-hydroxy-2, 5-bis[[(fluorenylmethyloxy)carbonyl]amino-1, 6-diphenylhexane To a solution of (2S,3S,5S)-2,5-diamino-3-hydroxy-1,6-diphenylhexane (2.84 g, 10.0 mmole; U.S. Pat. No. 5,354,866, issued Oct. 11, 1994) in $CH_2Cl_2$ (150 mL) was added Fmoc-OSu (NovaBiochem, 6.75 g, 20.0 mmole) and diisopropylethylamine (3.4 mL, 20 mmole). The solution was stirred at room temperature overnight. The solid formed was collected by filtration, washed five times with aqueous NaCl solution and dried under vacuum to give the first crop of product. The mother liquor was concentrated and the residue taken up in EtOAc (200 mL). The solution was washed with saturated NaCl (3×100 mL), then dried and filtered. Solvent evaporation gave additional product. Total yield was 6.13 g (84.2%). $^1$H NMR (DMSO-$d_6$): δ 1.60 (b.t. 2H), 2.50 (m, 2H), 2.55–2.80 (m, 4H), 3.65 (m, 1H), 3.8–4.2 (m, 9H), 7.05–7.45 (m, 18H), 7.60–7.70 (m, 4H), 7.86 (d, 4H). FAB-MS m/z 729 $(M+H)^+$.

EXAMPLE 4D

Allyl 10-{1'-[(2'S, 3"S, 5"S)-2", 5"-bis[[(fluorenylmethyloxy)carbonyl]amino]-1",6"-diphenyl-hex-3-yloxy]ethoxy}decanoate To a suspension of the product of Example 4C (3.28 g, 4.5 mmole) in $CH_2Cl_2$ (300 mL) was added allyl 10-vinyloxydecanoate (1.7 g, 6.7 mmole), followed by pyridinium p-toluenesulfonate (0.113 g, 0.45 mmole). The mixture turned clear in about an hour. The reaction was monitored frequently by TLC (40% EtOAc-hexane). Additional linker allyl 10-vinyloxydecanoate was added (~20% each time) if necessary until complete conversion of the starting core was observed. The solution was then washed with pH7.0 $Na_2HPO_4$ (0.1M) buffer (2×150 mL), saturated NaCl (2×100 mL), then dried ($MgSO_4$). Filtration and solvent evaporation gave a clear oil which was chromatographed on a silica gel column, using 40% EtOAc-hexane solvent to give a foamy solid, 3.0 g, 67%. $^1$H NMR (DMSO-$d_6$): δ 1.20–1.35 (m, 10H), 1.48 (m, 2H), 1.60–1.70 (m, 4H), 2.32 (t, 2H), 2.60–2.95 (m, 4H), 3.30–3.45 (m, 2H), 3.60–3.70 (m, 1H), 3.90–4.45 (m, 9H), 4.58 (d.t, 2H), 4.60–4.70 (m, 2H), 4.80–5.00 (m, 1H), 5.20–5.35 (d.d.d, 2H), 5.85–6.00 (m, 1H), 7.05–7.45 (m, 18H), 7.60–7.70 (m, 4H), 7.85 (d, 4H). FAB-MS (with $K^+$) m/z 1021, $(M+K)^+$.

EXAMPLE 5

10-{1'-[(2'S, 3"S, 5"S)-2", 5"-bis[[(fluorenylmethyloxy)carbonyl]amino]-1", 6"-diphenyl-hex-3-yloxy]ethoxy}decanoic acid To a solution of the product of Example 4D (4.8 g, 4.9 mmole) in 200 mL of anhydrous THF (Aldrich Gold Label) was added dimedone (6.85 g, 49 mmol) and tetrakis(triphenylphosphine)palladium (0) (0.56 g, 0.49 mmole). The solution was purged with nitrogen, then stirred under nitrogen at room temperature overnight. The solution was then concentrated and the residue was taken up in EtOAc (200 mL) and washed with pH7.0 $Na_2HPO_4$ (0.1M) buffer (2×150 mL). The organic solution was then treated repeatedly by mixing with saturated $NaHSO_3$ (150 mL) followed by vigorous stirring for 15–30 minutes until essentially all dimedone was removed (2–3 treatments required). The organic solution was then washed with saturated NaCl (2×150 mL) and worked up routinely. The crude product was purified by column chromatography using 50% EtOAc-hexane solvent, which afforded 3.8 g of white solid (84.0%). $^1$H NMR (CDCl$_3$): δ 1.20–1.35 (m, 10H), 1.48 (m, 2H), 1.65–1.75 (m, 4H), 2.32 (t, 2H), 2.60–2.95 (m, 4H), 3.30–3.45 (m, 2H), 3.60–3.70 (m, 1H), 3.90–4.45 (m, 9H), 4.60–4.70 (m, 2H), 4.75–4.90 (d.d, 1H), 7.05–7.45 (m, 18H), 7.60–7.70 (m, 4H), 7.85 (d, 4H). FAB-MS (with K$^+$) m/z 981, (M+K)$^+$.

EXAMPLE 6

Coupling of the Diamino Diol Core or the Diamino Alcohol Core to MBHA Resin

The modified diamino diol core (i.e., the product of Example 3) (5.0 mmole, ~1.5 eq. relative to the resin) or the modified diamino alcohol core (i.e., the product of Example 5) (5.0 mmole, ~1.5 eq. relative to the resin) was dissolved in 10 mL of N-methylpyrrolidone (NMP) and 10 mL of $CH_2Cl_2$. To the solution was added diisopropylcarbodiimide (0.79 mL, 5.0 mmole) and 0.68 g of HOBt. After stirring for 30–60 min., the solution was mixed with 5.0 g of NovaBead MBHA resin (NovaBiochem, La Jolla, Calif., substitution: 0.65 mmole/gram) which was pretreated with NMP. The mixture was shaken overnight and then filtered. The resin was washed with NMP (5 times), NMP/$CH_2Cl_2$ (1:1) mixture (5 times) and $CH_2Cl_2$ (5 times), and vacuum dried. The actual loading level was then determined based on the observed weight gain to be 0.5–0.55 mmole per gram.

TABLE 1

| Example | | A. Mono-ol (X = H) IC$_{50}$ (nM)[a] | B. Diol (X = OH) IC$_{50}$ (nM)[a] |
|---|---|---|---|
| 7 | O=C(CH(CH$_2$))NH-C(=O)-NH (hydantoin) | <1 | 9.6 |
| 8 | H$_2$N-C(=N)-S-CH=C-CH$_2$— (aminothiazole) | <1 | 12 |
| 9 | 3,4,5-trimethoxybenzyl (H$_3$CO, H$_3$CO, OCH$_3$) | <1 | 3.4 |
| 10 | pyridyl-thiomethyl (N=C-S-CH$_2$) | <1 | 16 |

Ph = phenyl
[a]The IC$_{50}$ against HIV-1 protease was measured according to the method described in U.S. Pat. No. 5,354,866, issued October 11, 1994.

EXAMPLES 7A–10A (X=H)

Automated Solid Phase Synthesis of Compounds Containing the Diamino Alcohol Core The automated solid phase synthesis was carried out on the Abimed AMS422 Multiple Peptide Synthesizer. For the synthesis of each compounds, 60–70 mg (~0.03 mmole) of the diamino alcohol resin (i.e., the product of Example 6) was added to six separate reaction vessels. The instrument software was then modified and solutions of the reagents and monomers prepared, all according to the instrument operation manual. A 20 v % solution of piperidine in NMP was used for removal of the Fmoc (deprotection) and activation of carboxylic acids was accomplished by in situ formation of HOBt ester with PyBOP (benzotriazol-1-yloxyltripyrrolidinophosphonium hexafluorophosphate) in the presence of N-methylmorpholine (NMM). The resins were first washed with NMP (3×1.5 mL), deprotected by two treatments with the piperidine solution (20 min. each time) and then washed with NMP (6×1.5 mL); A solution of Fmoc-Val in NMP (0.3 mL, ~0.24 mmole), a solution of PyBOP in NMP (0.22 mL, ~0.22 mmole) and a solution of NMM (0.1 mL, ~0.4 mmole) were delivered to each of the six reaction vessels. The mixture was then allowed a coupling time of 60 min. The coupling was then repeated for the second time (double coupling). Then deprotection and washing were repeated as described above. To each reaction vessel was then delivered a solution of following carboxylic acids in NMP, respectively: (5-hydantoin)acetic acid, (2-amino-4-thiazole)acetic acid, (3,4,5-trimethoxylphenyl) acetic acid, and (2-pyrimidylthio)acetic acid. A solution of PyBOP in NMP (0.22 mL, ~0.22 mmole) and a solution of NMM (0.1 mL, ~0.4 mmole) were delivered to each of the six reaction vessels. The mixture was then allowed a coupling time of 60 min. The coupling was then repeated for the second time (double coupling). After the final coupling, resins were washed with NMP (6×1.5 mL each reaction vessel) and $CH_2Cl_2$ (6×1.5 mL each reaction vessel ) and dried. The resins were then cleaved by treating the resins with 30% TFA in methylene chloride for 3 hours . Solutions of the released compounds were then evaporated in a speedvac and the products characterized by TLC and FAB-MS. The mass spectra were consistent with the assigned structures.

EXAMPLES 7B–10B (X=OH)

Automated Solid Phase Synthesis of Compounds Containing the Diamino Diol Core

The automated solid phase synthesis was carried out on the Abimed AMS422 Multiple Peptide Synthesizer. For the synthesis of each compound, 60–70 mg (~0.03 mmole) of the diamino diol resin (i.e., product of Example 6) was added to six separate reaction vessels. The instrument software was then modified and solutions of the reagents and monomers prepared, all according to the instrument operation manual. A 20 v % solution of piperidine in NMP was used for removal of the Fmoc (deprotection) and activation of carboxylic acids was accomplished by in situ formation of HOBt ester with PyBOP (benzotriazol-1-yloxyltripyrrolidinophosphonium hexafluorophosphate) in the presence of N-methylmorpholine (NMM). The resins were first washed with NMP (3×1.5 mL), deprotected by two treatments with the piperidine solution (20 min. each time) and then washed with NMP (6×1.5 mL); A solution of Fmoc-Val in NMP (0.3 mL, ~0.24 mmole), a solution of PyBOP in NMP (0.22 mL, ~0.22 mmole) and a solution of NMM (0.1 mL, ~0.4 mmole) were delivered to each of the six reaction vessels. The mixture was then allowed a coupling time of 60 min. The coupling was then repeated for the second time (double coupling). The deprotection and washing were repeated as described above. To each reaction vessel was then delivered a solution of the following carboxylic acids in NMP, respectively: 5-hydantoinacetic acid, 2-amino-4-thiazoleacetic acid, 3,4,5-trimethoxyphenylacetic acid, and (2-pyrimidylthio)acetic acid. A solution of PyBOP in NMP (0.22 mL, ~0.22 mmole) and a solution of NMM (0.1 mL, ~0.4 mmole) were delivered to each of the six reaction vessels. The mixture was then allowed a coupling time of 60 min. The coupling was then repeated for the second time (double coupling). After the final coupling, resins were washed with NMP (6×1.5 mL each reaction vessel) and $CH_2Cl_2$ (6×1.5 mL each reaction vessel) and dried. The resins were then cleaved by treating the resins with 95% aqueous TFA overnight . Solutions of the released compounds were then evaporated in a speedvac and the products characterized by TLC and FAB-MS. The mass spectra were consistent with the assigned structures.

The foregoing is merely illustrative of the invention and is not intended to limit the invention to the disclosed compounds and processes. Variations and changes which are obvious to one skilled in the art are intended to be within the scope and nature of the invention which are defined in the appended claims.

What is claimed is:

1. A compound of the formula:

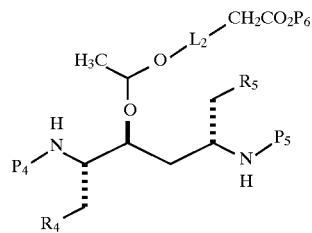

IIB wherein $R_4$ and $R_5$ are independently selected from phenyl, substituted phenyl, loweralkyl and cycloalkyl;

$L_2$ is
(a) alkylene,
(b) —O—$((CH_2)_2$—O$)_m CH_2$— wherein m is 1—10 or

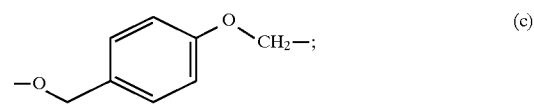

(c)

$P_4$ and $P_5$ are the same or different N-protecting groups; and $P_6$ is hydrogen or a carboxy protecting group.

2. A compound according to claim 1 wherein $R_4$ and $R_5$ are phenyl and $L_2$ is —$(CH_2)_p$— wherein p is 1–10 or —O—$((CH_2)_2$—O$)_m$—$CH_2$— wherein m is 2–6.

3. A compound according to claim 1 wherein $R_4$ and $R_5$ are phenyl, $L_2$ is —$(CH_2)_9$— or —O—$((CH_2)_2$—O$)_2$—$CH_2$— and $P_4$ and $P_5$ are independently selected from 9-fluorenylmethoxycarbonyl, allyloxycarbonyl and (2-trimethylsilyl)ethoxycarbonyl and $P_6$ is hydrogen or allyl.

4. A compound selected from the group consisting of:

Allyl 10-{1'-((2'S, 3"S, 5"S)-2",5"-bis(( (fluorenylmethyloxy)carbonyl)amino)-1",6"-diphenyl-hex-3-yloxy)ethoxy}decanoate and 10-{1'-((2'S, 3"S, 5"S)-2", 5"-bis(((fluorenylmethyloxy)carbonyl)amino) -1", 6"-diphenyl-hex-3-yloxy)ethoxy}decanoic acid.

* * * * *